(12) United States Patent
Bolmer

(10) Patent No.: US 6,288,294 B1
(45) Date of Patent: Sep. 11, 2001

(54) PURIFICATION OF HCFC-133A

(75) Inventor: Michael S. Bolmer, Lower Providence, PA (US)

(73) Assignee: Atofina Chemicals, Inc., Phila., PA (US)

(*) Notice: Subject to any disclaimer, the term of this patent is extended or adjusted under 35 U.S.C. 154(b) by 0 days.

(21) Appl. No.: 09/800,315

(22) Filed: Mar. 6, 2001

(51) Int. Cl.⁷ ...................................................... C07C 17/38
(52) U.S. Cl. .......................................... 570/177; 570/178
(58) Field of Search ...................................... 570/177, 178

(56) References Cited

FOREIGN PATENT DOCUMENTS 2318350    4/1998   (GB) .

*Primary Examiner*—Alan Siegel

(57) ABSTRACT

A method for purifying a 133a product mixture containing olefinic impurities is provided wherein the mixture is contacted with a diene under conditions sufficient to convert the olefinic impurities to cyclohexenes.

3 Claims, No Drawings

PURIFICATION OF HCFC-133A

BACKGROUND OF THE INVENTION

This invention relates to a method for purifying a chemical mixture containing olefinic impurities, more particularly to purifying a 1,1,1-trifluoro-2-chloroethane ("HCFC-133a" or "133a") product mixture containing olefinic impurities of the formula $CF_3CX=CYCF_3$, where X and Y are independently selected from H, Cl and F. HCFC-133a is used as an intermediate in the manufacture of 1,1,1,2-tetrafluoroethane ("HFC-134a" or "134a"), trifluoroethanol and pharmaceutical products. The aforementioned olefinic impurities have been found to reduce the activity of fluorination catalysts used to convert 133a to 134a. Also, the toxicity of these olefins makes them undesirable impurities in pharmaceuticals. The boiling points of these impurities are close to that of 133a, making them difficult to separate by distillation.

UK Patent Application 2318350 discloses a process to remove olefinic impurities from 133a by photochlorination to produce heavy (high-boiling) compounds. However, the quartz or glass reactors required for such a process are vulnerable to attack by the HF used in a fluorochemicals plant as a fluorinating agent. The photochlorination reaction also produces some 1,1,1-trichloro-2,2-dichloroethane ("123"), which causes a yield loss, and some HCl. A separate method must be used to remove the light (low boiling) impurities (HCl and unreacted chlorine from the photochlorination) and to remove the heavy compounds. Thus, it would be useful to find a simpler, more efficient method for removing olefinic impurities from 133a.

BRIEF SUMMARY OF THE INVENTION

A method of purifying a 133a product mixture containing olefinic impurities of the formula $CF_3CX=CYCF_3$ ("Formula I"), where X and Y are independently selected from H, Cl and F, is provided, which method comprising contacting the mixture with a diene such as 1,3-pentadiene under conditions sufficient to convert olefinic impurities to cyclohexenes.

DETAILED DESCRIPTION

It has now been found that olefinic impurities of Formula I can be converted to higher boiling, functionalized cyclohexenes by reaction with dienes and that the 133a product can then be readily separated from the high boiling cyclohexenes (and diene reactant) by conventional methods such as distillation or phase separation.

The impure 133a product typically contains one or more Formula I impurities such as $CF_3CH=CClCF_3$, $CF_3CCl=CClCF_3$, $CF_3CH=CHCF_3$ and $CF_3CH=CFCF_3$.

Any diene, such as isoprene, 1,3-pentadiene or 1,3-butadiene can be used as the diene reactant. While 1,3-butadiene is illustrated in the example to follow, higher boiling dienes such as isoprene or 1,3-pentadiene are preferred for ease of separation from 133a via distillation. A wide range of reaction conditions can be employed, but it is desirable to employ a pressure sufficient to keep the reactants in the liquid phase at the reaction temperature employed. Some typical conditions are as follows: temperatures from about 20° C. to about 150° C. (preferably about 50° C.–100° C.); pressures from about atmospheric to about 600 psig (preferably about 60–200 psig); contact time from about 30 seconds to 6 hours; diene to olefin mole ratio of from about 1:1 to 100:1 (preferably from 1:1 to 10:1); stirred or tubular reactors; batch or continuous reactions; separation of 133a from high boiling dienes and cyclohexenes via distillation or phase distillation. The reaction and separation can be conducted simultaneously in a separation device such as a distillation column, with the impure 133a being introduced at or near the bottom of the column while the diene is introduced at or near the top of the column, so that the converted impurities can be removed as formed. A high boiling polymerization inhibitor can optionally be employed to prevent dimerization of the diene.

The practice of the invention is illustrated in more detail in the following non-limiting example using a crude 133a product mixture containing about 7.2 weight % $CF_3CH=CHCF_3$ and about 6.2 weight % $CF_3CH=CFCF_3$. An autoclave was loaded with 10 grams of this crude product and 10 grams of 1,3-butadiene, then slowly heated to about 49° C. and held for one-half hour. Analysis of the products by gas chromatography-mass spectroscopy showed that about 84% of the $CF_3CH=CHCF_3$ and about 47% $CF_3CH=CFCF_3$ had been converted to higher boiling cyclohexene derivatives ($C_8H_8F_6$ and $C_8H_7F_7$, respectively).

What is claimed is:

1. A method of purifying a 1,1,1-trifluoro-2-chloroethane product mixture containing olefinic impurities of the formula $CF_3CX=CYCF_3$, where X and Y are independently selected from H, Cl and F, which method comprises contacting said mixture with a diene under conditions sufficient to convert olefinic impurities to cyclohexenes.

2. A method of purifying a 1,1,1-trifluoro-2-chloroethane product mixture containing olefinic impurities of the formula $CF_3CX=CYCF_3$, where X and Y are independently selected from H, Cl and F, which method comprises contacting said mixture with a diene selected from the group consisting of isoprene and 1,3-pentadiene under conditions sufficient to convert olefinic impurities to cyclohexenes.

3. A method of purifying a 1,1,1-trifluoro-2-chloroethane product mixture containing olefinic impurities of the formula $CF_3CX=CYCF_3$, where X and Y are independently selected from H, Cl and F, which method comprises contacting said mixture with a diene under conditions sufficient to convert olefinic impurities to cyclohexenes, said method being conducted in a separation device so that the converted impurities can be separated as formed.

* * * * *